US010265328B2

(12) United States Patent
Windisch

(10) Patent No.: US 10,265,328 B2
(45) Date of Patent: Apr. 23, 2019

(54) C-19 STEROIDS FOR SPECIFIC THERAPEUTIC USES

(75) Inventor: Martin Windisch, Bad Krozingen (DE)

(73) Assignee: Procima GmbH, Erlangen (DE)

( * ) Notice: Subject to any disclaimer, the term of this patent is extended or adjusted under 35 U.S.C. 154(b) by 598 days.

(21) Appl. No.: 12/734,616

(22) PCT Filed: Nov. 12, 2008

(86) PCT No.: PCT/EP2008/009541
§ 371 (c)(1),
(2), (4) Date: May 16, 2011

(87) PCT Pub. No.: WO2009/062683
PCT Pub. Date: May 22, 2009

(65) Prior Publication Data
US 2011/0263547 A1    Oct. 27, 2011

Related U.S. Application Data

(60) Provisional application No. 61/002,817, filed on Nov. 13, 2007.

(30) Foreign Application Priority Data

Nov. 13, 2007  (EP) ..................... 07022016

(51) Int. Cl.
| | | |
|---|---|---|
| *A61K 9/00* | (2006.01) |
| *A61K 9/02* | (2006.01) |
| *A61K 9/20* | (2006.01) |
| *A61K 9/48* | (2006.01) |
| *A61K 45/06* | (2006.01) |
| *A61K 47/06* | (2006.01) |
| *A61K 47/10* | (2017.01) |
| *A61K 47/14* | (2017.01) |
| *A61K 47/18* | (2017.01) |
| *A61K 47/26* | (2006.01) |
| *A61K 47/32* | (2006.01) |
| *A61K 47/36* | (2006.01) |
| *A61K 31/568* | (2006.01) |

(52) U.S. Cl.
CPC .......... *A61K 31/568* (2013.01); *A61K 9/0014* (2013.01); *A61K 9/0019* (2013.01); *A61K 9/02* (2013.01); *A61K 9/2018* (2013.01); *A61K 9/2059* (2013.01); *A61K 9/4858* (2013.01); *A61K 9/4866* (2013.01); *A61K 45/06* (2013.01); *A61K 47/06* (2013.01); *A61K 47/10* (2013.01); *A61K 47/14* (2013.01); *A61K 47/18* (2013.01); *A61K 47/26* (2013.01); *A61K 47/32* (2013.01); *A61K 47/36* (2013.01)

(58) Field of Classification Search
CPC ... A61K 31/568; A61K 2300/00; A61K 45/06
USPC ............................... 514/171, 177
See application file for complete search history.

(56) References Cited

U.S. PATENT DOCUMENTS

| | | | | |
|---|---|---|---|---|
| 2,762,818 | A * | 9/1956 | Levy ....................... | C07J 1/00 552/614 |
| 4,598,072 | A * | 7/1986 | Schweikert ............ | A61K 31/57 514/170 |
| 4,895,715 | A * | 1/1990 | Neri ...................... | A61K 31/565 514/171 |
| 5,824,326 | A | 10/1998 | Crotty et al. | |
| 5,904,931 | A | 5/1999 | Lipp et al. | |
| 6,242,436 | B1 * | 6/2001 | Llewellyn ............... | 514/177 |
| 6,586,417 | B1 | 7/2003 | Abraham | |
| 8,258,123 | B2 * | 9/2012 | Windisch ................ | A61K 8/63 514/171 |
| 9,114,163 | B2 * | 8/2015 | Teichmann .......... | A61K 31/568 |
| 9,138,477 | B2 * | 9/2015 | Teichmann .......... | A61K 31/568 |
| 2003/0199487 | A1 * | 10/2003 | Abraham ............... | A61K 31/56 514/178 |
| 2003/0229063 | A1 * | 12/2003 | Llewellyn .............. | A61K 31/57 514/178 |
| 2006/0018937 | A1 | 1/2006 | Friedman et al. | |
| 2009/0111784 | A1 * | 4/2009 | Teichmann .......... | A61K 31/568 514/171 |
| 2010/0061975 | A1 * | 3/2010 | Teichmann .......... | A61K 31/568 424/130.1 |
| 2010/0256102 | A1 * | 10/2010 | Windisch ................ | A61K 8/63 514/171 |

FOREIGN PATENT DOCUMENTS

| | | |
|---|---|---|
| DE | 44 05 898 | 8/1995 |
| EP | 0 307 135 | 3/1989 |

(Continued)

OTHER PUBLICATIONS

Doughlas et al.*

(Continued)

*Primary Examiner* — Sabiha N Qazi
(74) *Attorney, Agent, or Firm* — Locke Lord LLP; Scott D. Wofsy; Nicholas J. DiCeglie, Jr.

(57) ABSTRACT

The present invention relates to novel uses of C-19 steroid compounds, in particular C-19 steroids having an androsten-17-($OR_4$)-3-one structure for prophylactic and/or therapeutic uses, wherein $R_4$ is hydrogen or an unsubstituted or substituted alkyl, aryl, acyl or any group leading to hydroxyl upon biological metabolization or chemical deprotection. The present invention particularly relates to selected C-19 steroids displaying properties of high binding affinity to androgen receptor to block dihydrotestosterone from binding, while at the same time providing anabolic effects, which is useful for certain applications The therapeutic applications particularly include concepts based on influencing or controlling collagen and related therapeutic aspects, as well as concepts making use of certain disclosed effects the mentioned C-19 steroid compounds based on blocking the androgen receptor (AR) against binding of the natural androgen, dihydrotestosterone (DHT), while primarily circumventing a direct aromatase-inhibiting effect, The present invention also describes a pharmaceutical composition comprising a combination of such a compound and dimethyl isosorbide.

6 Claims, No Drawings

(56) References Cited

FOREIGN PATENT DOCUMENTS

| GB | 2 100 601 | * | 1/1983 |
|---|---|---|---|
| JP | 62-132810 | | 6/1987 |
| JP | 2003519182 A | | 6/2003 |
| JP | 2003534279 A | | 11/2003 |
| JP | 2006-306816 | | 11/2006 |
| WO | WO-92/05763 | | 4/1992 |
| WO | WO-92/07586 | | 5/1992 |
| WO | WO-01/23405 | * | 5/2001 |
| WO | WO-03/026568 | | 4/2003 |
| WO | WO-2005/042741 | | 5/2005 |
| WO | WO-2005/062760 | | 7/2005 |
| WO | WO-2006/084312 | | 8/2006 |
| WO | WO-2007/131736 | | 11/2007 |
| WO | WO-2007/131737 | | 11/2007 |

OTHER PUBLICATIONS

Davies et al. (abstract of J Enzyme Inhib. 1992; 6(2):141-7).*
Li X et al. (abstract of Steroids. Jun. 1995; 60(6):430-41).*
Oh et al. (UROLOGY 62:99-104, 2003).*
Raynaud et al., "Screening for anti-hormones by receptor studies", Journal of Steroid Biochemistry 6: 615-622.1975.
Harrison et al., "Gonadotropin-releasing hormone and its receptor in normal and malignant cells", Endocrine-Related Cancer (2004) 11 725-748.
Liang et al., "Immunocytochemical Localization of Androgen Receptors in Human Skin Using Monoclonal Antibodies Against the Androgen Receptor", The Journal of Investigative Dermatology, vol. 100, No. 5, May 1993, pp. 663-666.
Meier et al., "Recombinant Human Chorionic Gonadotropin But Not Dihydrotestosterone Alone Stimulates Osteoblastic Collagen Synthesis in Older Men with Partial Age-Related Androgen Deficiency", The Journal of Clinical Endocrinology & Metabolism 89(6):3033-3041.
Flamm et al., "An Urodynamic Study of Patients with Benign Prostatic Hypertrohy Treated Conservatively with Phyto Therapy or Testosterone", Wiener Klinische Wochenschrift, 91(18), 1979, pp. 622-627 (German).
Flamm et al., "An Urodynamic Study of Patients with Benign Prostatic Hypertrohy Treated Conservatively with Phyto Therapy or Testosterone", Wiener Klinische Wochenschrift, 91(18), 1979, pp. 622-627, XP008089756, ISSN: 0043-5325 (Partial Translation).
Mitamura et al., "Determination Method for Steroid 5α-Reductase Activity Using Liquid Chromatography/Atmospheric Pressure Chemical Ionization-Mass Spectrometry", Analytical Sciences, Oct. 2005, vol. 21, pp. 1241-1244.
Itami et al., "Role of androgen in mesenchymal epithelial interactions in human hair follicle", Journal of Investigative Dermatology, Symp.Proc., 10(3), 2005, pp. 209-211 (English Abstract—PubMed).

Ando, et al., "Expression of mRNA for androgen receptor, 5α-reductase and 17β-hydroxysteroid dehydrogenase in human dermal papilla cells", British Journal of Dermatology, 141(5), 1999, pp. 840-845 (English abstract—Wiley InterScience).
Itami et al., "Mechanism of action of androgen in hair follicles", Journal of Dermatological Science, 7 Suppl., Jul. 1994, pp. 98-103, (English abstract—unboundMedline).
Viennet et al., "Contractile forces generated by striae distensae fibroblasts embedded in collagen lattices", Archives of Dermatological Research, 297(1), 2005, pp. 10-17 9English abstract—springer).
Natsch et al., "A Specific Bacterial Aminoacylase Cleaves Odorant Precursors Secreted in the Human Axilla*", The Journal of Biological Chemistry, vol. 278, No. 8, Issue of Feb. 21, 2003, pp. 5718-5727.
Beier et al., "Localization of steroid hormone receptors in the apocrine sweat glands of the human axilla", Histochemistry and Cell Biology, 123(1), 2005, pp. 61-65.
Labrie et al., "Intracrinology and the Skin", Hormone Research, 54(5-6), 2000, pp. 218-229 (English abstract—Hormone Research).
Imperato-McGinley et al., "The Androgen Control of Sebum Production. Studies of Subjects With Dihydrotestosterone Deficiency and Complete Androgen Insensitivity", Journal of Clinical Endocrinology and Metabolism, vol. 76, No. 2, 1993, pp. 524-528.
Akamatsu et al., "Control of Human Sebocyte Proliferation In Vitro by Testosterone and 5-Alpha-Dihydrotestosterone Is Dependent on the Localization of the Sebaceous Glands", Journal of Investigative Dermatology, 99(4), 1992, pp. 509-511 (English).
Kurata et al., "Intranuclear androgen concentrations in facial skin", Journal of Dermatological Science, 2(2), 1991, pp. 75 (English abstract—ScienceDirect).
Chinese Office Action dated Dec. 30, 2014, and English translation thereof, issued on corresponding Chinese Patent Application 200880115837.3.
Notification of Preliminary Objection Reasons, issued in corresponding Korean Patent Application No. KR 10-2010-7010503, dated Apr. 17, 2015.
H. Zia et al. "Cosolvency of Dimethyl Isosorbide for Steroid Solubility," Pharmaceutical Research, vol. 8m No. 4, p. 502-504, (1991).
Notice of Reason for Rejection, issued in corresponding Japanese Patent Application No. JP 2010-533487, dated Feb. 22, 2016.
Naslund et al., "A Review of the Clinical Efficacy and Safety of 5α-Reductase Inhibitiors for the Enlarged Prostate", Clinical Therapeutics, 29(1), 2007, pp. 17-25.
Korean Office Action dated Apr. 20, 2016, and English translation thereof, issued during the prosecution of corresponding Korean Patent Application No. 10-2016-7007505.

* cited by examiner

C-19 STEROIDS FOR SPECIFIC THERAPEUTIC USES

The present invention relates to novel uses of C-19 steroid compounds, in particular C-19 steroids having an androsten-17-(OR$_4$)-3-one structure for particular therapeutic uses, wherein R$_4$ is hydrogen or an unsubstituted or substituted alkyl, aryl, acyl or any group leading to hydroxyl upon biological metabolization or chemical deprotection. The present invention particularly relates to selected C-19 steroids displaying special properties useful for certain therapeutic applications. The therapeutic applications according to the present invention particularly include concepts based on influencing or controlling collagen and related therapeutic aspects, as well as concepts making use of certain disclosed effects the mentioned C-19 steroid compounds based on blocking the androgen receptor (AR) against binding of the natural androgen, dihydrotestosterone (DHT), while primarily circumventing a direct aromatase-inhibiting effect, as will be further described below.

Prior attempts to control or influence collagen-containing tissues in order to alleviate various body conditions include administration of direct inhibition of the enzymes aromatase and 5α-reductase. The pharmaceutical inhibition of 5α-reductase is a common means to treat or to prevent benign prostatic hyperplasia (BPH) and is used for prevention of prostate cancer.

Studying 5α-reductase and its tissue-specific expression nature in the context of DHT generation within the body has developed anti-androgens and non-steroidal selective androgen receptor modulators (SARMs) to influence testosterone and dihydrotestosterone levels. Only cells expressing this enzyme can provide themselves with sufficient amounts of DHT. For example, substances such as steroidal finasterid or non-steroidal bicalutamide or flutamide have been widely used. Bicalutamide can suppress the osteoporotic side effects of androgen deprivation therapy for prostate cancer but has no intrinsic anabolic effect. So far no substance is known able to extinguish the androgenic effects of DHT as far as possible or even completely, and have anabolic effects at the same time. The closest approximation to this goal consists in substances able to increase the weight of the levator ani muscle in castrated rats and increase only slightly the weight of the shrunken prostate.

The use of anabolic steroidal androgens is difficult since it is associated with hepatotoxicity, potential for prostate stimulation, virilizing actions and other side effects resulting from their cross-reactivity to related steroid receptors. If an anabolic SARM used to treat frailty or osteoporosis were of steroidal nature it should neither be aromatizable nor reducible at position C5 of the sterol skeleton. So far no SARM has been developed able to block androgenic effects caused by DHT (growth or loss of hair, exaggerated sebum production, growth of the prostate, growth of cancer cells) and in the same time exert anabolic effects like testosterone.

The object of the present invention therefore is to provide improved possibilities to a range of valuable applications in order to better control and influence conditions of collagen status of body regions containing collagen, and other pathologic or disease states associated with impaired hormone balance or hormone function.

In order to solve the object, the present invention provides C-19 steroid compounds for particular applications as set forth in the appended claims. In the framework of these applications, use is made of particular properties that have been found to be associated with the specifically selected C-19 steroid compounds.

Without being bound to a certain theory, the concept of the present invention is based on the following considerations.

The gene coding for the androgen receptor is situated on the x-chromosome. Since men possess only one x-chromosome, defects of this chromosome have dramatic consequences. An affected XY-fetus develops phenotypically into girl instead of a true boy.

The principal mammalian androgens are testosterone and its more potent metabolite dihydrotestosterone (DHT). The related androgen receptor (AR) is a large protein of at least 910 amino acids. Each molecule consists of a portion which binds the androgen, a zinc finger portion that binds to DNA in steroid sensitive areas of nuclear chromatin, and an area that controls transcription.

Testosterone diffuses from the circulation into the cytoplasm of any cell. Depending on the enzymes present in the cytoplasm and their activity some is metabolized to estradiol by aromatase, some reduces to DHT (5α-reductase), and some remains as testosterone (T). Both T and DHT can bind and activate the androgen receptor, though DHT does so with more potent and prolonged effect. As DHT (or T) binds to the receptor, a portion of the protein is cleaved. The AR-DHT combination dimerizes by combining with a second AR-DHT, both are phosphorylated, and the entire complex moves into the cell nucleus and binds to androgen response elements on the promoter region of androgen-sensitive target genes. The transcription effect is amplified or inhibited by coactivators or corepressors.

Androgens exert their effects by binding to the highly specific androgen receptor (AR). The receptor proteins have a well-defined domain organisation and high-resolution structures are available for the C-terminal ligand binding domain (LBD), with different agonist and antagonist ligands bound, and the zinc-finger DNA-binding domain (DBD).

Structural studies of the ligand-binding domain of several steroid receptors have revealed that the dynamic properties of the C-terminal helix 12 (H12) are the major determinant of the activation mode of these receptors. H12 exhibits high mobility and different conformations in the absence of ligand. Upon ligand binding, H12 is stabilized in a precise position to seal the ligand-binding pocket and finalize the assembly of the activation function (AF-2) domain. Antiandrogens can work by impeding repositioning of the mobile carboxyl-terminal helix 12 of the ligand binding pocket, which blocks the ligand-dependent transactivation function (AF-2) located in the AR ligand-binding domain.

The androgen receptor has been shown to contain two transactivation functions: one is represented by a structurally defined hydrophobic groove on the surface of the LBD, formed by residues from helices 3, 4, 5 and 12 (AF-2), while the other maps to the structurally flexible N-terminal domain (NTD) and is termed AF1. The main determinants for transactivation map to NTD. The NTD is potentially involved in multiple protein-protein interactions and the length of this domain has been positively correlated with the activity of AF1 for different members of the nuclear receptor superfamily.

All nuclear receptor superfamily members of eukaryotic transcriptional regulators contain a highly conserved activation function 2 (AF2) in the hormone binding carboxyl-terminal domain and, for some, an additional activation function 1 in the NH (2)-terminal region which is not conserved. The molecular basis of AF2 is hormone-dependent recruitment of LXXLL motif-containing coactivators to a hydrophobic cleft in the ligand binding domain. AF2 in the androgen receptor (AR) binds only weakly to LXXLL motif-containing coactivators and instead mediates an androgen-dependent interaction with the AR NH (2)-terminal domain required for its physiological function. Two α-helical regions mediate the androgen-dependent, NH (2)- and carboxyl-terminal interaction. FXXLF in the AR NH (2)-terminal domain mediates interaction with AF2 and is the predominant androgen-dependent interaction site. This FXXLF sequence and a second NH(2)-terminal WXXLF sequence interact with different regions of the ligand binding domain to stabilize the hormone-receptor complex and may compete with AF2 recruitment of LXXLL motif-containing coactivators. Testosterone is a weaker androgen than DHT because of less favourable T-dependent AR FXXLF and coactivators LXXLL motif interactions at AF2.

The ligand binding structures of the AR exhibit a certain flexibility of several residues buried in the ligand-binding pocket that can accommodate a variety of ligand structures. The ligand structure itself (dimension, presence, and position of unsaturated bonds that influence the geometry of the steroidal nucleus or the electronic properties of the neighbouring atoms, etc.) determines the number of interactions it can make with the binding domain. The geometry of the atoms forming electrostatic interactions at both extremities of the steroid nucleus seems mainly responsible for the higher affinity measured experimentally for DHT over testosterone. In contrast the androgenic steroid used in sport doping, tetrahydrogestrinone (THG) which possesses the highest affinity, establishes more van der Waals contacts with the receptor than the other steroids.

DHT has a flatter structure than testosterone and therefore fits better in the ligand binding pocket.

5α-reductase, the enzyme system that metabolizes testosterone into dihydrotestosterone, occurs in two isoforms. The type 1 isozyme is composed of 259 amino acids, has an optimal pH of 6-9 and represents the 'cutaneous type'; it is located mainly in sebocytes but also in epidermal and follicular keratinocytes, dermal papilla cells and sweat glands as well as in fibroblasts from genital and non-genital skin. The type 2 isozyme is composed of 254 amino acids, has an optimal pH of about 5.5 and is located mainly in the epididymis, seminal vesicles, prostate and fetal genital skin as well as in the inner root sheath of the hair follicle and in fibroblasts from normal adult genital skin. The genes encoding type 1 and type 2 isozymes are found in chromosomes 5p and 2p, respectively, and each consists of 5 exons and 4 introns.

The type 1 isozyme is not detectable in the fetus, is transiently expressed in newborn skin and scalp, and permanently expressed in skin from the time of puberty. The type 2 isozyme is transiently expressed in skin and scalp of newborns. Type 2 is the predominant isozyme detectable in fetal genital skin, male accessory sex glands, and in the prostate, including benign prostatic hyperplasia and prostate adenocarcinoma tissues. Both isozymes are expressed in the liver, but only after birth. Mutations in type 2 isozyme cause male pseudoliermaphroditism, and many mutations have been reported from various ethnic groups. Affected 46XY individuals have high normal to elevated plasma testosterone levels with decreased DHT levels and elevated testosterone/DHT ratios. They have ambiguous external genitalia at birth so that they are believed to be girls and are often raised as such. However, Wolffian differentiation occurs normally and they have epididymides, vas deferens and seminal vesicles. Virilization occurs at puberty frequently with a gender role change, probably. The prostate in adulthood is small and rudimentary, and facial and body hair is absent or decreased. Balding has not been reported. Spermatogenesis is normal if the testes are descended. The clinical, biochemical and molecular genetic analyses of 5α-reductase 2 deficiency highlight the significance of DHT in male sexual differentiation and male pathophysiology. Type 1 isoenzyme may play important roles in the androgen physiology of normally virilized males and may contribute to masculinization in type 2-deficient males at the time of puberty.

Also bone cells contain the type 1 isoenzyme. In vivo inhibition of the two isoenzymes can cause an elevated incidence of impotence, decreased libido, ejaculation disorders, and gynaecomastia. The bones remain unaffected.

The AR is widely distributed among reproductive and nonreproductive tissues, including the prostate and seminal vesicles, male and female external genitalia, skin, testis, ovary, cartilage, sebaceous glands, hair follicles, sweat glands, cardiac muscle, skeletal muscle and smooth muscle, gastrointestinal vesicular cells, thyroid follicular cells, adrenal cortex, liver, pineal, and numerous brain cortical and subcortical regions, including spinal motor neurons. This wide distribution of the receptor needs to be mapped with the particular type and concentration of cofactors that are present in each tissue and cell type. This will provide a more accurate picture of the potential nuclear receptor complex that can be assembled in each case after ligand activation.

In the present invention, a certain group of C-19 steroid compounds have surprisingly found to display significant positive effects useful for specific therapeutic uses which will be described in more detail below, in particular uses associated with collagen stabilization, augmentation and strengthening, as well as uses based on blocking the androgen receptor (AR) against binding of the natural androgen, dihydrotestosterone (DHT), while primarily circumventing a direct aromatase-inhibiting effect, as will be further described below. The C-19 steroid compounds selected according to the present invention for these beneficial uses are based on the property of a high binding affinity towards the androgen receptor (AR), yet diminishing androgenic activities typically via an effect of blocking naturally (body-) derived androgens such as testosterone and especially dihydrotestosterone (DHT) from the AR, while at the same time exerting anabolic activities on the target tissue and organs and their environmental conditions.

According to the present invention, the use may correspondingly be determined by selecting the C-19 steroid compound having both a blocking effect against a binding of DHT towards AR (measurable by binding studies against DHT as a reference compound), and an anabolic effect (measurable e.g. by determining an enhancement on collagen production of reference cells susceptible for such enhancement, such as fibroblasts). The use may be further determined by an administrated amount suitable for effecting AR binding and anabolic effect, and by an appropriate application condition, such as type of patient, or type of target site or organ being AR positive (i.e. having measurable androgen receptors) or being able to transport the aforementioned activities in vivo to the designated final target site or organ within a patient.

The compounds having a high potency in respect of diminishing or completely abolishing androgenic effects on biological pathways, while enhancing anabolic activities on the target sites, tissues and organs of particular relevance for therapeutic applications, such as adipose cells, fibroblasts, epithelial cells, basal cells, bone cells, gland cells and other cells of the prostate, gland cells and other cells of the breast, and other cells, as well as organs or bodies surrounding these cells have been surprisingly found to be associated with an androsten-17-ol-3-one structure exempting testosterone and dihydrotestosterone, wherein even more potent compounds to bring about the desired effects of the invention are further defined by a 1-en double bond and/or a 4-en double bond, and/or a substituent bonded to the 17-ol (hydroxyl) group within the common C-19 steroid structure.

In more preferred embodiments directed to select C-19 steroid compounds among the above-defined group of compounds which are even more potent for embodying the present invention, the C-19 steroid compound has, in addition to
(i) the blocking effect on AR combined with
(ii) the enhancement of anabolic activities,
the following effects or properties alone or in combination:
(iii) the compound is not aromatized by aromatase;
(iv) the compound is not reduced by 5α-reductase;
(v) the compound inhibits 5α-reductase;
(vi) in the form of its C-17 oxidized metabolite, the compound exhibits enhanced aromatase inhibition.

Each of the aforementioned properties (iii) to (vi) alone or in combination, when combined with the primary activities on AR blocking and anabolic enhancement, leads to a further replenishment or blocking of hormones or hormone-like metabolites, which would otherwise counteract the desired effects according to the invention. For example, when the selected compound is not metabolized by aromatase or 5α-reductase, or both, neither estrogens or estrogen-like metabolites nor androgenically active metabolites are generated at the target site, notably the cells, tissues and glands as well as related organs mentioned above, thereby further diminishing androgenic effects while enhancing anabolic effects. Exaggerated virilisations can be effectively diminished. Additional inhibition of 5α-reductase further reduces androgenic activities. Moreover, when the compounds of the present invention are oxidizable by 17β-hydroxysteroid-dehydrogenase after application in vivo, they can be converted into more potent aromatase inhibitors, thereby additionally modulating activities at the target site valuable for certain applications.

According to the present invention, the use may correspondingly be determined by selecting the C-19 steroid compound having the aforementioned effects or properties (iii) to (vi) alone or in combination. These effects or properties (iii) to (vi) can be measured by correspondingly known methods. The use may be further determined by a suitable administrated amount of the compound, and by an appropriate application condition, such as type of patient, or type of target site or organ enabling the aforementioned effects or properties (iii) to (vi) alone or in combination.

The steroidal nature of the compound of the present invention implicates some additional advantages. For example the quality to be converted intracellularily by 17β-hydroxysteroid dehydrogenase type 2 to a more potent steroidal aromatase-inhibitor. Furthermore, there is the potential ability to exert a negative feedback on the release of gonadotropins from the pituitary gland, especially in the case of 4-hydroxytestosterone or its salts or esters. Thus the production of sex hormones is further slowed down systemically. Since the compound by itself can display anabolic effects it can compensate for the loss of testosterone and assists to block DHT which is of particular value in cases of BPH and prostate cancer. In addition, a feedback-property achieved by the use according to the present invention will alleviate somewhat the tendency to develop gynecomastia if used during androgen receptor blocking therapy for prostate cancer by conventional treatments.

In addition, thanks to the steroid-type structure, the compound of the present invention exhibits hydrophobic properties, which may significantly assist topical administrations.

In a particular embodiment of the present invention, the compound is selected from compounds having the following formula:

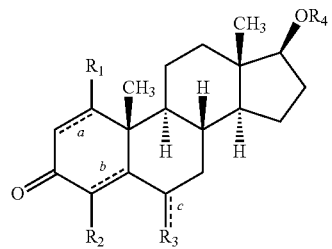

wherein
a, b and c respectively denote, independently from each other, a single bond or a double bond, with the proviso that at least one of a, b and c represents a double bond, and with the proviso that if a is a single bond and b is double bond $R_2$ is not H;
$R_1$ is hydrogen or $C_1$ to $C_6$ alkyl;
$R_2$ is hydrogen or $OR_5$, wherein $R_5$ is hydrogen or $C_1$ to $C_6$ straight chain or branched alkyl;
$R_3$ is, in case of c being a single bond, hydrogen or $C_1$ to $C_6$ alkyl, or in case of c being a double bond, $CHR_5$, wherein $R_5$ is the same as defined before;
$R_4$ is hydrogen, $C_1$ to $C_6$ alkyl, phenyl unsubstituted or substituted by $C_1$ to $C_6$ alkyl, $COR_6$ acyl group ($R_6$ being hydrogen; $C_1$ to $C_6$ straight chain or branched alkyl; phenyl or benzoyl respectively unsubstituted or substituted by $C_1$ to $C_6$ alkyl), or any group leading to hydroxyl upon biological metabolization or chemical deprotection; and salts thereof.

In terms of a preferable consistency of being surely not aromatized, yet ensuring strong affinity to AR while having potency for satisfying conditions (iv) to (vi) mentioned above, compounds are preferably selected wherein b is a double bond, $R_2$ is hydroxyl and/or $R_3$ is methylene group, and $R_4$ is hydrogen, $C_1$-$C_6$ alkyl or $C_1$-$C_6$ acyl group. Particularly preferred are 4,17β-dihydroxyandrost-4-en-3-one (4-hydroxytestosterone; 4OHT) (wherein a is single bond, b is double bond and c is a single bond, $R_2$ is OH and $R_4$ is hydrogen) and the corresponding esters (such as $R_4$ denoting $COR_6$ acyl group as defined) and salts.

In case of the particularly preferred compound according to the present invention, 4OHT and its salts and esters, further use can be made, if desired, from an effect which results in a negative feedback on gonadotropin secretion.

Compounds of the present invention also include those which are metabolized to the above-defined compounds.

Moreover, it preferred that compounds are used which have predominantly anabolic activities on target cells, rather than mere androgenic effects. Further preferable are compounds which also display apoptotic effects on target cells. All these effects have been found to be associated with 4-hydroxytestosterone (4OHT), and the same should correspondingly apply to esters and salts mentioned above.

Not only in theory but also in practice the compounds of the present invention and in particular 4-OHT and its related analogous compounds are the ideal anabolic substances. It remains as it is and it escapes aromatization or 5α-reduction.

In binding with higher affinity to the AR than DHT without substantially exerting or even banning the slightest androgenic effect, it prevents the binding of DHT to this receptor, yet its binding to the androgen receptor leads substantially or even exclusively to anabolic effects. This can be deduced from topical applications to the skin. In the skin areas over the buttocks it anabolically increases the concentration of collagen fibres.

Although EP0307135A may partly disclose some compounds which may fall under the aforementioned formula, its therapeutic concept deal with aromatase inhibition alone or, if related to a possible androgenic activity, with an inhibitory effect on estrogen biosysnthesis through a decrease in gonadotropin secretion (i.e. systemic effects, necessitating actions via generative glands, ovaries, LH-associated effects and the like). The concepts of the present invention however differ, and thus compounds are selected by distinctly different selection criteria in terms of effects exerted directly at the site of interest by considerations directed to, alone or in combination, receptor status of target cells or tissues; mode of administration; group of persons to be treated; and certain indicated uses. For example, in order to make use according to the present invention, improved effects are obtained if conditions are observed such as AR positive target cells or tissues, a preferred topical administration onto the skin or the mucosa, and treating and/or prophylactically acting against benign prostate hypertrophy, prostate carcinoma (possibly supplemented to a conventional therapy), collagen-associated disorders; osteoporosis, women undergoing hormone replacement therapy, and mastalgia. A disclosure of U.S. Pat. No. 2,762,818A does not go beyond using 4-hydroxytestosterone and its esters to treat an androgen deficiency status itself as a medical implication. No mention is made of the fact that the substitution at C-4 prevents both aromatization to estrogens or impedes virilizing effects to this substance brought about by 5α-reduction to DHT. These metabolic possibilities immanent to testosterone were not known at this time (1956). There was neither a purpose nor a finding which would suggest an androgen-blocking activity from which the uses according to the present invention could have been deduced. Further, US2003/0229063A addresses low androgen to estrogen ratios in men (leading to endocrine disorders) and only for this purpose attempts to make use of 4-hydroxytestosterone based on an asserted direct aromatase-inhibiting effect alone in the purpose to reduce estrogen levels.

In WO 2005/062760 incorporated herein in its entirety by way of reference, possible roles of androgen receptor (AR) in prostate carcinogenesis and breast cancer is discussed, and methods for breast cancer diagnosis by assaying the presence of AR are presented. However, in terms of therapeutic concepts, WO 2005/062760 is limited to control AR itself not androgen mediated activity, in the context of mammary gland development by inhibiting AR activity. Moreover, US 2003/0199487A1 seeks to gradually increase androgen levels for the promotion of fat free mass and athletic performance without side effects associated with DHT, via 4-hydroxyandrostenedione metabolite and 4-androstenedione precursor hormone.

The compounds used according to the present invention preferably have a binding affinity to the androgen receptor (AR) higher than DHT; more preferably the binding affinity is high by having affinity specific to AR in a range of $IC_{50} \leq 500$ nM, preferably $IC_{50} \leq 100$ nM and more preferably $IC_{50} \leq 50$ nM, wherein $IC_{50}$ is defined as the concentration of the compound required to reduce specific binding of a reference compound, 5α-dihydrotestosterone (DHT), by 50%. The $IC_{50}$-values can be determined by known methods using radioactively labelled DHT as reference compound, for example by a standard dextran-coated charcoal adsorption method as described by Raynaud et al., J. Steroid Biochem. 6, 615-622 (1975), using 1 nM reference concentrations of radiolabeled [$^3$H]-DHT, or by similar $IC_{50}$ determination methods described in the literature. Because the concentration of AR in the target cell is very low, typically in the nanomolar range approximately, differences in binding constants to the order contemplated in the present invention are significant.

If not known from other information or data, receptor status of target cells or target tissues with respect to AR and possibly other receptors can be determined and, if desired, quantified by standard methods known to the person skilled in the art, including immunoassays involving AR-specific or other receptor-specific antibodies, DNA and/or RNA hybridization assays or PCR amplification tests involving AR-specific or other receptor-specific nucleic acid probes.

The compounds according to the invention shall be used in amounts effective against the indicated conditions. "Use" according to the present invention may include method of treatment or prophylaxis by the specified compounds, or of a composition containing the same as an active principle together with a suitable carrier and/or diluent, for the described uses, and it includes use in the preparation of said compositions.

In experiments carried out with the compounds of the present invention it could be shown that they had excellent skin penetration capabilities so that the desired effect could be achieved by simple topic administration of e.g. an ointment, lotion or cream etc. comprising an effective amount of a compound according to the present invention to an area of a patient in need of treatment. After topical administration, the compound(s) penetrate through the skin and concentrate in the fatty tissue. In preferred embodiments, the compound of the present invention is combined with a skin penetration enhancer.

A particularly preferred compound of the present invention, 4-hydroxytestosterone, is disclosed in e.g. U.S. Pat. No. 2,762,818 A and commercially available (e.g. from Bulk Nutrition, Graham, N.C., USA—see bulknutrition.com for further information; WINKOS GmbH D-79189 Bad Krozingen, Del.). The derivatives, in particular salts and esters of the preferred 4,17β-dihydroxyandrost-4-ene-3-one include suitable ester groups, such as straight chain, branched chain or cyclic or aromatic acyl groups like formyl, acetyl, propionyl, butyryl, pentanoyl, hexanoyl, heptanoyl and benzoyl, but are not limited thereto. The esters can be formed with the 4 and/or 17 hydroxy group, preferably with the 17 hydroxy group. Its salts and esters can also be prepared by known methods (see e.g. U.S. Pat. No. 2,762,818 A).

The compounds and preparations or compositions of the invention can be administered in a variety of forms, e.g. topically, in the form of an ointment, a cream, a lotion, a gel, a spray, a powder, an oil or a transdermal plaster, also comprising depot usage forms (including pellets); orally, in the form of tablets, capsules, sugar or film coated tablets, liquid solutions or suspensions: rectally, in the form of suppositories; parenterally, e.g. intramuscularly, or by intravenous injection or infusion. According to a preferred embodiment, the compounds of the invention are designed for topical administration.

The applied amount depends on the age, weight, conditions of the user and administration form; for example the dosage adopted for oral administration to adult humans may range from about 10 to about 150-1000 mg per application, from 1 to 5 times daily.

The invention includes preparations or compositions comprising a compound of the invention in association with a carrier or diluent.

For topical use, the composition may be formulated by including, for example, vegetable oils and fats such as almond oil, peanut oil, olive oil, peach kernel oil, castor oil; plant extracts; ethereal oils; furthermore vegetable waxes and synthetic and animal oils; fats and waxes such as stearic acid and stearate esters, lauric acid and lauric esters, sorbitane esters, ceterayl alcohols; lecithin, lanolin alcohols, carotene, fragrances, mono- or polyhydric alcohols, urea, surfactants such as Proloxamers, Tweens, and the like; preservatives and colorants etc. Formulation as an oil-in-water or water-in-oil emulsion is preferred.

Solid oral forms may for example contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatine, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. These preparations may be manufactured in known manner, for example, by means of mixing, granulating, tabletting, sugar-coating, or film-coating processes. The liquid dispersions for oral use may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The active compound content of a suitable composition can be between 0.0001 and 20% by weight, preferably 0.6% until 10% by weight, further preferably 1 and 5% by weight, of the compound according to the invention. A customary range is 0.6 to 5% by weight.

If substances are admixed to promote skin penetration, their content, when using hyaluronidases, can be, for example, between 0.01 and 1% by weight, preferably 0.05 and 0.2% by weight, when using dimethylisosorbide or DMSO between 1 and 25% by weight, preferably 5 and 10% by weight.

In a particular embodiment of the present invention, the compounds described above are formulated in a suitable topical administration form together with a suitable solvent.

As a particularly effective solvent in terms of excellent solubility for the type of compounds according to the present invention, combined with effectively assisting epithelial penetration thereof, has been found by dimethylisosorbide (also called Arlasolve DMI; available by ICI), alone or in combination with other carriers or solvents, for example alcohols or polyols such as ethanol, polyethylene glycol, propylene glycol and mixtures thereof, and possibly other ingredients described above.

If desired, the effects described above can be supplemented by additionally using a 5α-reductase inhibitor in an effective amount sufficient to inhibit 5α-reductase, and/or an anti-androgen or SARM in an amount effective to block AR. In this respect, 5α-reductase inhibitors such as finasterid, 6-azasteroids and other compounds known to inhibit 5α-reductase of type 1 or type 2, or to dually inhibit both type 1 and type 2 can be used in combination with the compounds described above. Further, an anti-androgen known as such can be used in combination, such as bicalutamide or flutamide. According to the present invention SARM is understood to be comprised within the term of known anti-androgens.

In the following, preferred but non-limiting embodiments are presented, where the compounds according to the present invention can display their effects in particularly effective fields of application.

Benign Prostatic Hyperplasia (BPH)

Benign prostatic hyperplasia (BPH) is a noncancerous enlargement of the prostate gland that may restrict the flow of urine from the bladder. Cellular accumulation and gland enlargement may be due to epithelial and stromal proliferation, impaired preprogrammed cell death (apoptosis), or both. Cellular alterations that include changes in proliferation, differentiation, apoptosis and senescence in the epithelium and stroma are implicated in BPH pathogenesis. Molecular analyses have yielded numerous candidate genes important in disease progression. Differential expression of cytokines and growth factors in BPH tissue suggests roles for inflammation and hypoxia. More recently, the voiding dysfunction that ensues from prostate gland enlargement and bladder outlet obstruction (BOO) has been generically termed lower urinary tract symptoms (LUTS). These entities overlap; not all men with BPH have LUTS, and, likewise, not all men with LUTS have BPH. The same can be said for BOO.

BPH involves both the stromal and epithelial elements of the prostate arising in the periurethral and transition zones of the gland; the condition is considered a normal part of the aging process in men.

The prostate is a walnut-sized gland that forms part of the male reproductive system. The gland is composed of several regions or lobes that are enclosed by an outer layer of tissue (capsule). The different zones are the peripheral, central, anterior fibromuscular stroma, and transition. The transition zone, which surrounds the urethra, enlarges with age in a hormonally dependent manner. Castrated males do not develop BPH. In the past, chronic end-stage BOO often led to renal failure and uremia. While this complication is much less common now, chronic BOO secondary to BPH may lead to urinary retention, renal insufficiency, recurrent urinary tract infections, gross hematuria, and bladder calculi. BPH is a common problem affecting the quality of life (QOL) for approximately 75% of men over the age of 50 and 90 percent of men in their 70s and 80s have had some symptoms of BPH. Histologic evidence of BPH occurs in up to 90% of men by age 80 years. Worldwide, approximately 30 million men have symptoms related to this benign enlargement.

BPH is a progressive disease. Progression can become evident in several ways: a worsening of LUTS, a decrease in urinary flow, continued growth of the prostate, acute urinary retention, need for surgery, bladder complications, hematuria, and recurrent urinary tract infections. These events generally cause a worsening of the patient's quality of life. This disease can be prevented for several reasons. First, in most men, BPH is a progressive disorder; left alone, over time the prostate grows larger, urinary flow becomes impeded and voiding symptoms increase. Second, BPH progression can lead to BPH disease in certain men at risk.

Third, men at risk can be identified by elevated serum levels of PSA, generally 1.5 ng/ml or higher, reflecting a prostate volume of 30-40 cc or greater. Fourth, 5α-reductase inhibiting drugs can lower intraprostatic DHT, the major culprit of BPH and thereby prevent BPH disease in men at risk. Efficacy does not appear related to symptoms, only to prostate volume, as reflected by a serum PSA level >1.5 ng/ml.

It has been estimated that circulating testosterone (T) declines longitudinally from age 19 at an average rate of 1% per year. The free or dialyzable fraction of serum T and the bioavailable (the sum of free fraction and loosely bound to albumin fraction) T decline more rapidly with age. Decreased values of testosterone in plasma and a poor response to gonadotropins demonstrate a diminished synthesizing capacity of the testes in old men. The decreased testosterone plasma values are followed by an increase in LH. The response of the anterior pituitary gland to LH-RH stimulation in old men is normal. Under basal conditions estrone as well as estradiol plasma concentrations increase significantly with age because of increased conversion from androgens. Parallel to estrogen plasma values an increased concentration of the sexual hormone binding globulin (SBHG) is found, resulting in a steep decrease of the free (=active) testosterone fraction. Decreased testosterone, which is more strongly bound to SHBG and increased estrone and estradiol plasma values result in an androgen/estrogen imbalance in old men.

BPH stroma shows 2-3 times higher 5α-reductase activity than epithelium. In BPH the prostate contains twice as much DHT than a normal gland. Most of it is found in nuclear fractions, whereby the nuclear DHT content of BPH stroma is significantly higher than that of BPH epithelium. In addition, nuclei of BPH stroma contain significantly more estradiol than epithelial nuclei. The androgen receptor is evenly distributed between epithelium and stroma of BPH, while the estrogen receptor is preferably assayed in BPH stroma. Intraprostatic estrogens and their receptors are elevated and concentrated in the stroma. BPH stroma apparently is not only a preferential tissue for 5α-reductase activity and DHT enrichment but also for nuclear estradiol accumulation.

The precursor of androgens as well as of estrogens originate from the cortex of the adrenals. The major product is DHEA (no side-chain anymore). DHEA is present in for mammals unusually high concentrations. It can permeate the membranes of all cells. Depending on the different enzymes present within the cell it can end up as testosterone or estradiol. The key precursor is androstenedione, which is made intracellularily from DHEA in a single step. This step as well as the following steps is accelerated by LH. Receptors for LH are present in normal prostate and hyperplastic prostate. Increased LH (in ageing men) may contribute to the increased concentration of DHT in the prostate. The local production of DHT and estradiol is of crucial importance for BPH. In human BPH no clear evidence exists on the modulatory effect of estrogens on bFGF, KGF and TGFbeta formation. A western diet, characterized by high fat consumption, predisposes men to BPH, while a diet rich in flavonoids and lignanes, containing phyto-estrogens, lowers this risk. These data suggest that in the medical treatment of BPH, antiestrogens or aromatase inhibitors may be used: however, up to now the clinical results of this treatment are not promising and the improvement of the obstructive symptoms does not exceed that of placebo. A possible explanation of this unsatisfactory result could be that the estrogen reduction secondary to the use of aromatase inhibitors is counterbalanced by the rise of androgen precursors.

Compounds selected according to the present invention are ideal for prevention of BPH, as they possess the following characteristics in common: inhibition of 5-alpha-reductase; blocking of the androgen receptor against DHT; ability to exert a negative feedback on secretion of gonadotropins; and inhibition of aromatase, in particular after it has been oxidized at C-17 in vivo. All these characteristics are most effectively found in 4-hydroxytestosterone, and this correspondingly applies to its salts and esters. Specifically, the inactivation of aromatase can occur through intracellular oxidation by 17-beta-hydrosteroid dehydrogenase type 2, which is present in the epithelia of the prostate. This is the manner the aromatase inhibitor should perform, since C-19 sterols are produced to a lesser extent, are only slowly reduced to DHT, and DHT cannot bind to the androgen receptor. This type of primary prevention using the harmless drug disclosed by the present invention could serve to any aged man.

The compound used according to the present invention can applied to the prostate also topically via a suppository. This local application may lead to high intraprostatic drug levels as well as to useful systemic drug levels.

Evidence of the association of finasteride with male breast cancer comes from the Medical Therapy of Prostatic Symptoms (MTOPS) study of about 3047 men. 4 breast cancers occurred, three of them in a group which received finasteride alone. The compounds of the present invention, in particular 4-hydroxytestosterone and its salts and esters rather prevent breast cancer than to provoke it. Thus, the compounds of the present invention can be used alone or in combination with conventional 5α-reductase inhibitors or anti-androgens such as finasteride in order to prevent or treat BPH.

Prophylaxis and/or Treatment of Prostate Cancer

There is no apparent increase in cancer rates in clinical trials of testosterone supplementation in normal men or men at increased risk for prostate cancer, no relationship of prostate cancer risk with serum testosterone levels in multiple longitudinal studies, and no reduced risk of prostate cancer in men with low testosterone. Low serum testosterone and a younger age predict for a poor outcome in metastatic prostate cancer.

Conventional strategies to prevent prostate cancer include dietary fat reduction and supplementation with vitamins D and E, and selenium. Pharmacological intervention so far comprises cyclo-oxygenease inhibitors, antiestrogens, and in particular 5-alpha reductase inhibitors. In the Prostate Cancer Prevention Trial a total of 18,882 men over 55 years with a PSA serum level less than 3.0 ng/ml were randomized to receive either finasteride 5 mg/day or placebo for 7 years. Despite a 25% reduction of prostate cancers in the treatment arm the results were discussed controversially. This criticism was mainly due to the observation of significantly more high-grade cancers in the finasteride group.

The antihormonal therapy of prostate cancer consists of androgen receptor blocking substances alone or in combination with GnRH analoga. These small peptides disrupt gonadotropin-secretion by the pituitary gland. The testis is then unable to produce testosterone. The conversion of DHEA into testosterone is theoretically maintained. In fact intraprostatic testosterone is only decreased about 75%, DHT about 90%.

Prior attempts by androgen receptor blocking substances are not detrimental for the bones but cause gynecomastia in 40% of the patients. GnRH analoga lead to osteoporosis. After a while the carcinoma is able to grow independently from androgens.

If the carcinoma is localized, "watchful waiting" is a treatment option. It is only reasonable for patients aged 70 and older with low-risk tumors or those aged 80 years and older with medium-risk tumors. With watchful waiting doctors actively and carefully monitor the patient for signs that the cancer has worsened, treating symptoms of the disease when they occur. During this phase PSA, the size of the gland and histology have to be monitored.

Within the concept of the present invention, this watchful waiting can valuably be supplemented by administration of the compound of the invention. This compound and in particular 4-hydroxytestosterone can block the androgen receptor, inhibit 5α-reductase and lower gonadotropin levels. In this manner, gynecomastia phenomena can be additionally alleviated.

Because of virtually absent undesired effects the compounds of the invention can accompany any other therapy at any stage of the prostate cancer disease. In case of watchful waiting it is most suitably used as a topical formulation onto the skin or the mucosa respectively affected by the disease. It is also most suitably formulated as a suppository.

A further promising concept is based on a comparative evaluation between DHT and the compounds of the present invention. DHT is able to abolish the growth of certain breast cancer cells in culture, whereas 4-hydroxytestosterone has been shown to be even more effective. It is credible that 4-hydroxytestosterone and its analogous compounds is able to retard the growth of prostate cancer cells since DHT inhibits the proliferation of a variant of the human prostate cancer cell line LNCaP. This effect may readily hold also true for hormone independent cancer.

Gynecomastia Associated with Prostate Cancer

Men consuming substantial amounts of anabolic steroids (e.g. bodybuilders and general fitness exponents) paradoxically they grow often female like breasts though their body-fat is reduced at around 8-10-percent (normal 15%). Only steroids giving rise to estradiol or estrone can generate these "bitch tits". Gynecomastia is a common situation, with a proliferation of glandular component of male breast secondary to an imbalance in sexual hormones in mammary tissue. Anabolic steroid administration for prolonged periods may cause an excess of circulating estrogens through the conversion of testosterone to estrogens. A prominent estrogen effect on the breast may produce breast enlargement since both estrogen- and androgen-receptors are present in gynecomastia tissue. The preference of the breast tissue indicates that aromatase in men is preferentially expressed in the breast tissue. Conventionally, DHT in topical preparations is used to control gynecomastia. Apparently the androgen receptor conveys a defense against local accumulation of body fat.

Conventional androgen blockers used in the therapy of prostatic carcinoma also cause gynecomastia (as monotreatment they cause gynecomastia in about 49% of the patients, whereas in combination with GnRH agonists this drops to 20%). GnRH agonists by themselves have caused gynecomastia in 9% of the patients. This indicates that increased testosterone levels as in bodybuilders together with increased LH cause gynecomastia since LH stimulates local production of estrogens. Apparently GnRH agonists cause gynecomastia by themselves, since neither testosterone nor LH is increased. The substrate for this local testosterone production most likely is DHEA. LH receptors are present in many tissues such as the skin and the breast. GnRH receptors are also present in the breast (Harrison et al., Endocr Relat Cancer. 11(4):725-748 (2004)). Conventionally, gynecomastia has also been treated systemically with either the nonsteroidal aromatase inhibitor letrozole or the selective estrogen receptor modulator tamoxifen. Only treatment by estrogen receptor modulation/blocking has shown some success. This indicates that the potential of aromatase-inactivation inherent e.g. to 4-hydroxytestosterone would not be of major importance for the treatment of gynecomastia of patients undergoing prostate cancer treatment.

As the compounds used according to the present invention have shown anabolic activities without being themselves androgenic, it is reasonable that alleviating effects against gynecomastia in patients, who undergo prostate cancer treatment by AR blocking drugs, proceeds via negative feedback control of gonadotropin secretion by pituitary gland and thus, eventually, reduces levels of LH systemically and estrogens locally. This particularly applies to 4-hydroxytestosterone and its salts and esters.

Control of Collagen

Cellulite is a problem resulting from unstable subcutaneous structure and especially the region at or between adipose tissue and cutis tissue. In order to stabilize these structures, structural proteins and elastic fibers are relevant factors, and usually fibroblast cells are involved in generating such structural proteins and fibers.

It has been found that due to the presence of androgen receptors, at least partially, at relevant target cells involved in the formation of cellulite and other affected subcutaneous tissue, one can make effective use of the dual activity associated with the compounds of the present invention, namely binding to AR without however having a substantial androgenic effect, while on the other hand displaying anabolic activities on relevant target cells such as fibroblasts. Selecting the preferred steroids according to the present invention thus blocks AR against the effects of naturally derived androgens such as DHT, while preferably stimulating the generation of structural proteins and elastic fibers and in particular collagen synthesis via their anabolic effect.

Androgen receptors have been found to be present in human skin (see e.g. Liang et al., J. Invest. Dermatol. 1993, 100(5), pp. 663-666 (1993)). Furthermore, the better androgenic effects can be blocked, the more pronounced is a stimulation of anabolic effects and notably collagen formation (based on an observation made e.g. by Meier et al. in J. Clin. Endocrinol. Metab. 89(6), pp. 2033-241 (2004).

The observation that the topical treatment of the skin over the predilection areas of cellulite with a preparation containing 4-OHT leads within four weeks to a considerable solidification of the skin confirms that this preparation has an anabolic effect. The mechanism underlying this strengthening of the skin apparently is a drastic augmentation of collagen fibres in the skin accompanied by a marked diminution and shrinkage of the adipocytes entrapped in the mesh of collagen fibres. Cellulite exhibits a diffuse pattern of extrusion of underlying adipose tissue into dermis. The border between the two layers is made up of collagen fibres. Strengthening this border by increasing its collagen content by stimulating the fibroblasts to produce more collagen leads to a marked improvement of the appearance of cellulite.

A topical formulation containing a compound according to the present invention such as 4-OHT or an analogous compound can increase the collagen content of the skin via stimulation of the fibroblasts. A topical formulation containing 4-OHT has proven to be superior than 4-OHA. It is reasonable to assume that 4-OHT has solely anabolic effects. After application to the skin no androgenic effect whatsoever could be observed in this highly androgen-sensitive organ. Apparently is 4-OHT unable to exert any androgenic effects such as hair growth or pimples.

Beneficial effects can likewise be assumed for application cases where strengthening, stabilisation and/or augmentation of collagen is at issue too, i.e. also applications to the skin for purposes other than cellulite.

Correspondingly, there are envisaged according to the present invention prophylactic applications and/or treatments where collagen and other supportive proteins may play a significant role, such as applications to ligaments, fasciae, tendons, cartilages, bones, dentine and the vessel walls of arteries, veins and urinary passageways. Likewise, the compounds of the present invention are valuable for the prophylaxis and/or treatment of myocardial infarction and brain infarction; osteoporosis; arteriosclerosis; urinary incontinence; for the amelioration of sun exposure to the skin; without being limited thereto.

Osteoporosis; Hormone Replacement Therapy (HRT) in Women

Recently the hormone replacement therapy for postmenopausal women has been discredited because it allegedly favors the development of breast cancer. Although the compounds disclosed by the present invention and in particular 4-hydroxytestosterone are presumed to be rather antiestrogenic via their intracellular conversion into to enhanced aromatase inhibitor through oxidation at C-17, their anabolic effects on muscle and bones can beneficially alleviate osteoporosis.

In addition, the highly potent aromatase inhibition character after being intracellularly converted into the C-17 oxidized form within the breast and its ability to reduce the size of estrogen receptor positive as well as the majority of estrogen receptor negative breast cancers render the compounds of the present invention very suitable for prevention of postmenopausal osteoporosis. The hallmark of the postmenopausal state is the constant elevation of gonadotropins. Since many tissues and organs possess LH receptors it is likely that, without prophylaxis and/or treatment with the compound disclosed by the present invention, local conversion of DHEA into estrogens or androgens depending on the predominant enzymatic activity is strongly increased. It is conceivable that some of the other complaints accompanying menopause are due to this fact.

The diagnostic hallmark of osteoporosis is decreased density of the bones in x-rays. Therapy so far focuses on remineralization. If there is no collagen however, there is nothing to remineralize. Therefore attempts should be made not to slow down the decomposition of the bones but to actively support the production of collagen within the bone. Osteoporosis is hardly due to blockage of the functions of the androgen receptor which convey the pure androgenic effects. XY women (CAIS) have no bone problems. Bicalutamide as the by far most used substance for therapeutic blockage of the androgen receptor has only slightly negative effects on bone. Steroidal aromatase-inactivators have less direct consequences for the bones than nonsteroidal aromatase inhibitors, since both can give rise to anabolic compounds.

To this end, the compounds disclosed in the present invention and in particular 4-hydroxytestosterone and its analogous compounds are ideal, since they display anabolic effects and no true androgenic effects, which are the adverse effects feared to be a consequence of anabolic therapies. Additionally it blocks androgenic effects associated with bodily derived DHT. This makes it the ideal anabolic treatment for aged persons of either gender independent of HRT.

Based on the rationale of the present invention, the compounds disclosed like 4-hydroxytestosterone have an additional beneficial effect in postmenopausal women, given their ability to exert a negative feedback on the secretion of gonadotropins by pituitary gland. Alternatively, it is possible to complement conventional HRT with a view towards breast cancer prevention and exerting anabolic effects. Breast cancer can be more safely prevented by such a supplement of HRT.

Mastalgia

Mastalgia affects up to two-thirds of women at some time during their reproductive lives. It is usually benign, but the fear of underlying breast cancer is why many women present for evaluation. Mastalgia can be associated with premenstrual syndrome, fibrocystic breast disease, psychologic disturbance and, rarely, breast cancer. Approximately 15% require pain-relieving therapy. Noncyclic mastalgia responds poorly to systemic treatment but resolves spontaneously in up to 50% of cases.

Danazol is the only FDA-approved hormonal treatment and has been used in cyclic form to limit the adverse effects. Being less effective than tamoxifen, danazol has variety of effects. It prevents the midcycle surge of luteinizing hormone (LH) and follicle-stimulating hormone (FSH), but it does not significantly suppress basal LH or FSH in gonadally intact human beings. In castrated animals it can prevent the compensatory increase in LH and FSH. Danazol binds to androgen, progesterone, and glucocorticoid receptors but does not bind to estrogen receptors. It binds to sex hormone-binding globulin and corticosteroid-binding globulin, inhibits multiple enzymes of steroidogenesis and increases the metabolic clearance rate of progesterone. It is known that metabolites of danazol are hormonally active. Other biological properties of danazol, besides its primary one of suppression of gonadotropic effect, are related to its androgenicity.

Moreover, 4-hydroxytestosterone and analogous compounds according to the present invention achieve shrinkage of adipose tissue, certainly not by androgenic affects. As they have pronounced anabolic effects, it is likely that such effects are responsible for the reduction of adipose tissue which may further contribute to a reduction of internal pressure to the breast tissue and thus relief of pain.

Based on the widespread effects elucidated for the compounds of the present invention, in particular 4-hydroxytestosterone and its analogous compounds, mastalgia is a very promising and tailored for such a target disorder. Especially due to being oxidized within the breast cells to even more potent aromatase inhibitors, combined with a highly potential negative feedback control on gonadotropin secretion in the pituitary gland and consecutively lowering of levels of LH systemically and finally estrogens locally will provide a particularly effective relieving activity against mastalgia. All these activities contribute to low local estrogen levels in the affected female breast.

The present invention is further illustrated by the description of the following examples, which are however only for illustrative purposes and shall not be understood in any limiting manner.

EXAMPLE 1

The compound of the present invention can be synthesized as follows.

In a first step, 2.5 g testosterone is dissolved in 100 ml cold MeOH. After adding 9 ml NaOH (2%) and 17 ml $H_2O_2$ (30%) the mixture is stirred for 24 h at 4° C. The resulting epoxids are precipitated with ice-water. In a second step, 2 g of the dry epoxids are dissolved in 200 ml acetic acid containing 2% $H_2SO_4$. The solution is stirred for 4 h at room temperature. The reaction products are precipitated with ice-water. Thereafter, the reaction products are washed with 1% NaOH solution to hydrolyse the acetyl esters. The total yield of pure 4-hydroxtestosterone is in the range of 40-50%.

EXAMPLE 2

A cream for topical administration according to the invention can be formulated in conventional manner using the following amounts of ingredients. The amounts are given per 100 g of cream:

| | |
|---|---|
| 4-hydroxy-17β-acetyl-androst-4-en-3-one | 4.5 g |
| cetearyl alcohol | 7.5 g |
| paraffin wax | 3.0 g |
| sodium carbomer | 2.5 g |
| isopropyl myristate | 6.0 g |
| sorbitan monostearate | 1.0 g |
| polysorbate 20 | 3.0 g |
| stearyl alcohol | 2.0 g |
| dimethyl isosorbital (Arlasolve DMI) | 5.0 g |
| purified water ad | 100.0 g |

The resulting cream can be given topically on the skin or mucosa above a body region of a human affected by a disease to be treated, such as BPH or prostate cancer. It can be given three times per day in this manner. The topic administration can be combined with a therapy using conventional other 5α-reductase inhibitors or anti-androgens.

EXAMPLE 3

A gel can be formulated in conventional manner using the following amounts of ingredients. The amounts are given per 100 g of gel:

| | |
|---|---|
| 4-hydroxytestosterone | 2.5 g |
| ethanol 95% in water | 70.0 g |
| carbopol 980 | 0.5 g |
| isopropyl myristate | 2.5 g |
| triethanolamine | 0.5 g |
| purified water ad | 100.0 g |

The resulting gel can be given topically on the body region affected by (i.e. for therapeutic treatment), or suspected to be affected by (i.e. for prophylactic treatment) osteoporosis.

EXAMPLE 4

A composition is prepared by mixing the following constituents per 100 g total weight:

| | |
|---|---|
| 4-hydroxytestosterone | 7.5 g |
| dimethyl isosorbide (Arlasolve DMI) | 15.0 g |
| ethanol 95% in water | 15.0 g |
| purified water ad | 100.0 g |

The composition can be used topical application onto the breast of a women affected by mastalgia.

4-hydroxy-17β-acetyloxy-androst-4-ene-3-one (17-acetyl ester of 4-hydroxytestosterone) can be used instead of 4-hydroxatestosterone in the amount indicated.

EXAMPLE 5

Tablets each weighing 0.150 g and containing 25 mg of the active substance, can be manufactured as follows (composition for 10000 tablets):

| | |
|---|---|
| 4,17β-dihydroxyandrost-4-ene-3-one | 250 g |
| lactose | 800 g |
| corn starch | 415 g |
| talc powder | 30 g |
| magnesium stearate | 5 g |

The 4,17β-dihydroxyandrost-4-ene-3-one, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets. The tablets can be used orally for prophylactically or therapeutically treating a man undergoing prostate cancer therapy by conventional 5α-reducatase or anti-androgen drugs such as finasterid, to thereby alleviate or reduce the risk of gynecomastia.

EXAMPLE 6

Capsules, each dosed at 0.200 g and containing 20 mg of the active substance can be prepared (composition for 500 capsules):

| | |
|---|---|
| 4,17β-dihydroxyandrost-4-ene-3-one | 10 g |
| lactose | 80 g |
| sorn starch | 5 g |
| magnesium stearate | 5 g |

This formulation is encapsulated in two-piece hard gelatine capsules and dosed at 0.200 g for each capsule. The tablets can be used orally for strengthening collagen-containing tissues like vessel walls, to thereby reduce the risk of myocardial infarction, brain infarction and arteriosclerosis.

EXAMPLE 7

An ointment for topical administration according to the invention can be formulated in conventional manner using the following amounts of ingredients. The amounts are given per 100 g of ointment:

| | |
|---|---|
| 17β-hydroxy-6-methylenandrost-1,4-diene | 2.5 g |
| propylene glycol | 25.0 g |
| isopropyl myristate | 6.0 g |
| sorbitan monostearate | 1.0 g |

| | |
|---|---|
| polysorbate 80 | 2.0 g |
| stearyl alcohol | 2.0 g |
| hyaluronic acid | 0.1 g |
| purified water ad | 100.0 g |

The resulting ointment can be given topically on the skin above tissue regions affected by a deficiency of collagen, such as weaknesses or other disorders of ligaments, fasciae, tendons, cartilages, or sites of arteriosclerosis.

EXAMPLE 8

An ointment for topical administration according to the invention can be formulated in conventional manner using the following amounts of ingredients. The amounts are given per 100 g of ointment:

| | |
|---|---|
| 4-hydroxy-17β-propionyloxy-androst-1,4-diene-3-one | 2.5 g |
| propylene glycol | 20.0 g |
| isopropyl myristate | 7.5 g |
| dimethyl isosorbide (Arlasolve DMI) | 10.0 g |
| stearyl alcohol | 5.0 g |
| purified water ad | 100.0 g |

The ointment can be given topically on the skin above tissue regions affected by phenomena of mastalgia. Diminution of a women's adipose breast tissue can assist in the alleviation of mastalgia.

EXAMPLE 9

A composition for injection according to the invention can be formulated using the following amounts of ingredients:

| | |
|---|---|
| 4,17β-dihydroxyandrost-4-ene-3-one | 10.0 mg |
| benzyl alcohol | 5.0 mg |
| polysorbate | 25.0 mg |
| sodium chloride | 10.0 mg |
| purified and sterilized water ad | 1 ml |

The thus prepared composition is injected once a week close to osteoporotic bones.

EXAMPLE 10

A suppository formulation for a simultaneous topical pharmaceutical combination composition is formulated in conventional manner using the following amounts of ingredients. The amounts are given per 50 g of gel:

| | |
|---|---|
| 4-hydroxytestosterone | 2.75 g |
| finasterid | 1.25 g |
| glycerol gelatine | 20 g |
| PEG 400 | 11 g |
| cacao butter | 15 g |

The suppository can be applied rectally locally to the site affected by prostate cancer.

The invention claimed is:

1. A method for the treatment of androgen receptor positive prostate carcinoma, the method comprising administering to a patient a treatment effective amount of 4-hydroxytestosterone or a salt or ester thereof.

2. The method according to claim 1, further comprising administering the compound by topical application.

3. The method according to claim 1, further comprising obtaining
(i) a blocking effect on AR and
(ii) an enhanced anabolic activity.

4. The method according to claim 1, further comprising obtaining a negative feedback on gonadotropin secretion.

5. The method according to claim 1, further comprising administering the compound prior to, concurrent with or after prostate cancer treatment with another drug selected from the group consisting of a 5α-reductase inhibitor and an anti-androgen.

6. The method according to claim 1, further comprising administering a second compound selected from the group consisting of a 5α-reductase inhibitor and an anti-androgen.

\* \* \* \* \*